(12) United States Patent
Mangiardi et al.

(10) Patent No.: US 10,779,977 B2
(45) Date of Patent: Sep. 22, 2020

(54) VARIABLE SCALE STENT DEPLOYMENT DEVICE

(71) Applicant: QualiMed Innovative Medizinprodukte GmbH, Winsen (Luhe) (DE)

(72) Inventors: Eric K. Mangiardi, Charlotte, NC (US); Dennis L. Steffen, Tavernier, FL (US)

(73) Assignee: QUALIMED INNOVATIVE MEDIZINPRODUKTE GMBH, Winsen (Luhe) (DE)

( * ) Notice: Subject to any disclaimer, the term of this patent is extended or adjusted under 35 U.S.C. 154(b) by 204 days.

(21) Appl. No.: 15/981,349

(22) Filed: May 16, 2018

(65) Prior Publication Data
US 2018/0256379 A1   Sep. 13, 2018

Related U.S. Application Data

(63) Continuation of application No. 14/858,881, filed on Sep. 18, 2015, now Pat. No. 9,999,531, which is a continuation-in-part of application No. 12/545,982, filed on Aug. 24, 2009, now Pat. No. 9,439,652.

(51) Int. Cl.
| | |
|---|---|
| *A61F 2/966* | (2013.01) |
| *A61F 2/95* | (2013.01) |
| *A61B 17/12* | (2006.01) |
| *A61B 17/28* | (2006.01) |
| *A61B 90/00* | (2016.01) |

(52) U.S. Cl.
CPC ........ *A61F 2/966* (2013.01); *A61B 17/12022* (2013.01); *A61F 2/95* (2013.01); *A61B 17/2841* (2013.01); *A61B 2017/1205* (2013.01); *A61B 2090/061* (2016.02); *A61B 2090/0811* (2016.02); *A61F 2/9517* (2020.05); *A61F 2230/0069* (2013.01)

(58) Field of Classification Search
CPC ....... A61B 17/12022; A61F 2/95; A61F 2/966
See application file for complete search history.

(56) References Cited

U.S. PATENT DOCUMENTS

| | | | |
|---|---|---|---|
| 5,201,757 A | | 4/1993 | Heyn et al. |
| 5,370,134 A | | 12/1994 | Chin et al. |
| 5,449,372 A | * | 9/1995 | Schmaltz ................. A61F 2/88 604/104 |

(Continued)

FOREIGN PATENT DOCUMENTS

| | | |
|---|---|---|
| CN | 2652421 | 11/2004 |
| WO | 2002083037 | 10/2002 |
| WO | 2006072934 | 7/2006 |

OTHER PUBLICATIONS

File History of U.S. Appl. No. 12/545,982, filed Aug. 24, 2009.

(Continued)

*Primary Examiner* — Richard G Louis
(74) *Attorney, Agent, or Firm* — Ping Wang; Morris, Manning & Martin LLP

(57) ABSTRACT

A variable scale medical implant deployment device comprising a variable inner diameter scale sleeve insert is provided. Also described are kits containing the variable scale medical implant deployment device and methods for deploying a medical implant into a body lumen using a variable scale medical implant deployment device.

17 Claims, 16 Drawing Sheets

(56) References Cited

U.S. PATENT DOCUMENTS

| | | | |
|---|---|---|---|
| 5,571,168 | A | 11/1996 | Toro |
| 5,591,172 | A | 1/1997 | Bachmann et al. |
| 5,891,112 | A | 4/1999 | Samson |
| 5,968,052 | A | 10/1999 | Sullivan, III et al. |
| 6,077,258 | A | 6/2000 | Lange et al. |
| 6,143,021 | A | 11/2000 | Staehle |
| 6,383,211 | B1 | 5/2002 | Staehle |
| 6,413,269 | B1 | 7/2002 | Bui et al. |
| 6,530,933 | B1 | 3/2003 | Yeung et al. |
| 6,631,715 | B2 | 10/2003 | Kirn |
| 7,527,644 | B2 | 5/2009 | Mangiardi et al. |
| 7,547,321 | B2 | 6/2009 | Silvestri et al. |
| 2002/0052641 | A1 | 5/2002 | Monroe et al. |
| 2002/0111666 | A1 | 8/2002 | Hart et al. |
| 2003/0060813 | A1 | 3/2003 | Loeb et al. |
| 2004/0147877 | A1* | 7/2004 | Heuser .............. A61M 25/0662 604/165.02 |
| 2004/0153137 | A1 | 8/2004 | Gaschino et al. |
| 2005/0038495 | A1 | 2/2005 | Greenan |
| 2006/0135961 | A1 | 6/2006 | Rosenman et al. |
| 2007/0073247 | A1 | 3/2007 | Ewaschuk |
| 2007/0179586 | A1 | 8/2007 | Aguirre et al. |
| 2007/0233222 | A1 | 10/2007 | Roeder et al. |
| 2007/0250150 | A1 | 10/2007 | Pal et al. |
| 2008/0195041 | A1 | 8/2008 | Goldfarb et al. |
| 2008/0228258 | A1 | 9/2008 | Gerdts et al. |
| 2009/0118740 | A1 | 5/2009 | Mangiardi et al. |
| 2009/0192600 | A1 | 7/2009 | Ryan |
| 2009/0209914 | A1* | 8/2009 | Koch ................ A61M 39/0613 604/167.02 |
| 2011/0046710 | A1 | 2/2011 | Mangiardi et al. |
| 2012/0330331 | A1 | 12/2012 | Paul, Jr. et al. |
| 2016/0008153 | A1 | 1/2016 | Mangiardi et al. |

OTHER PUBLICATIONS

File History of U.S. Application No. 14/858,881, filed Sep. 18, 2015.

Extended European Search Report of Application No. 15904296.9 dated Apr. 2, 2019.

* cited by examiner

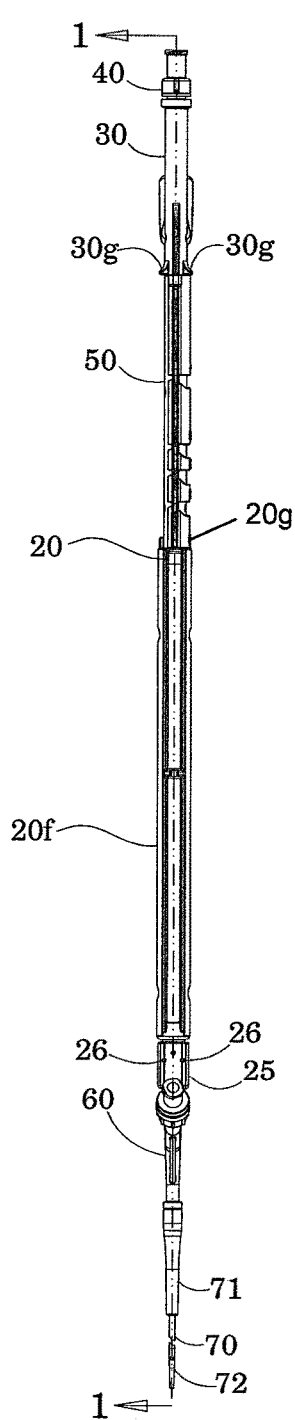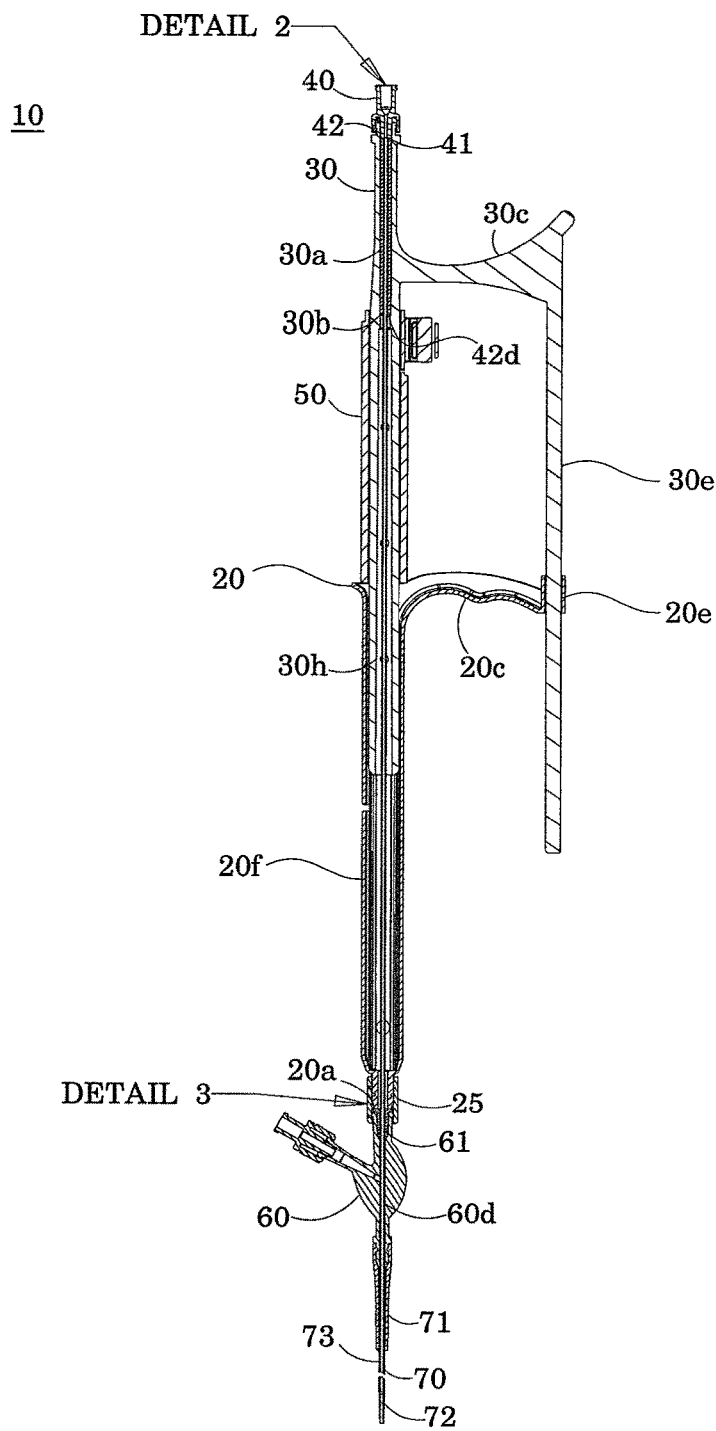
FIG. 2A
FIG. 2B
SECTION 1-1

DETAIL 3

DETAIL 2

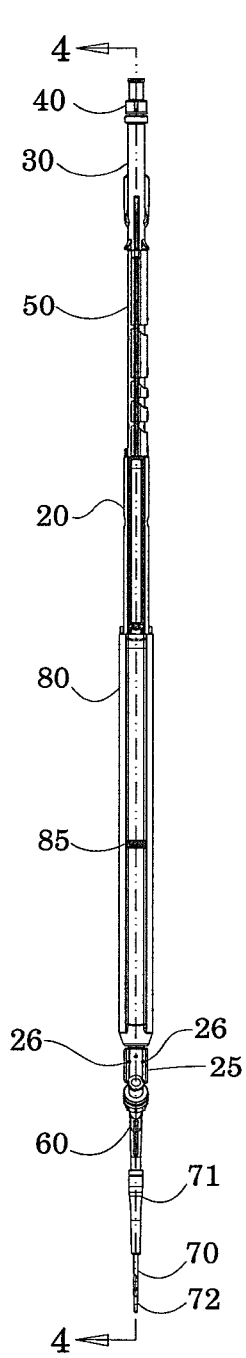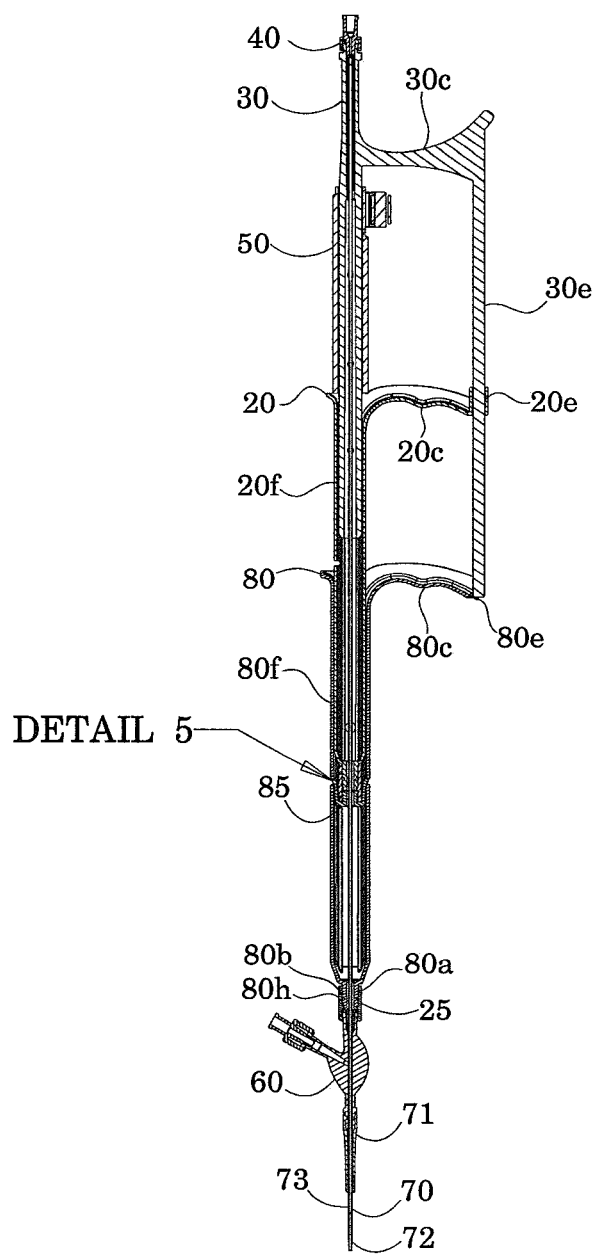
FIG. 12A
SECTION 4-4
FIG. 12B

DETAIL 5

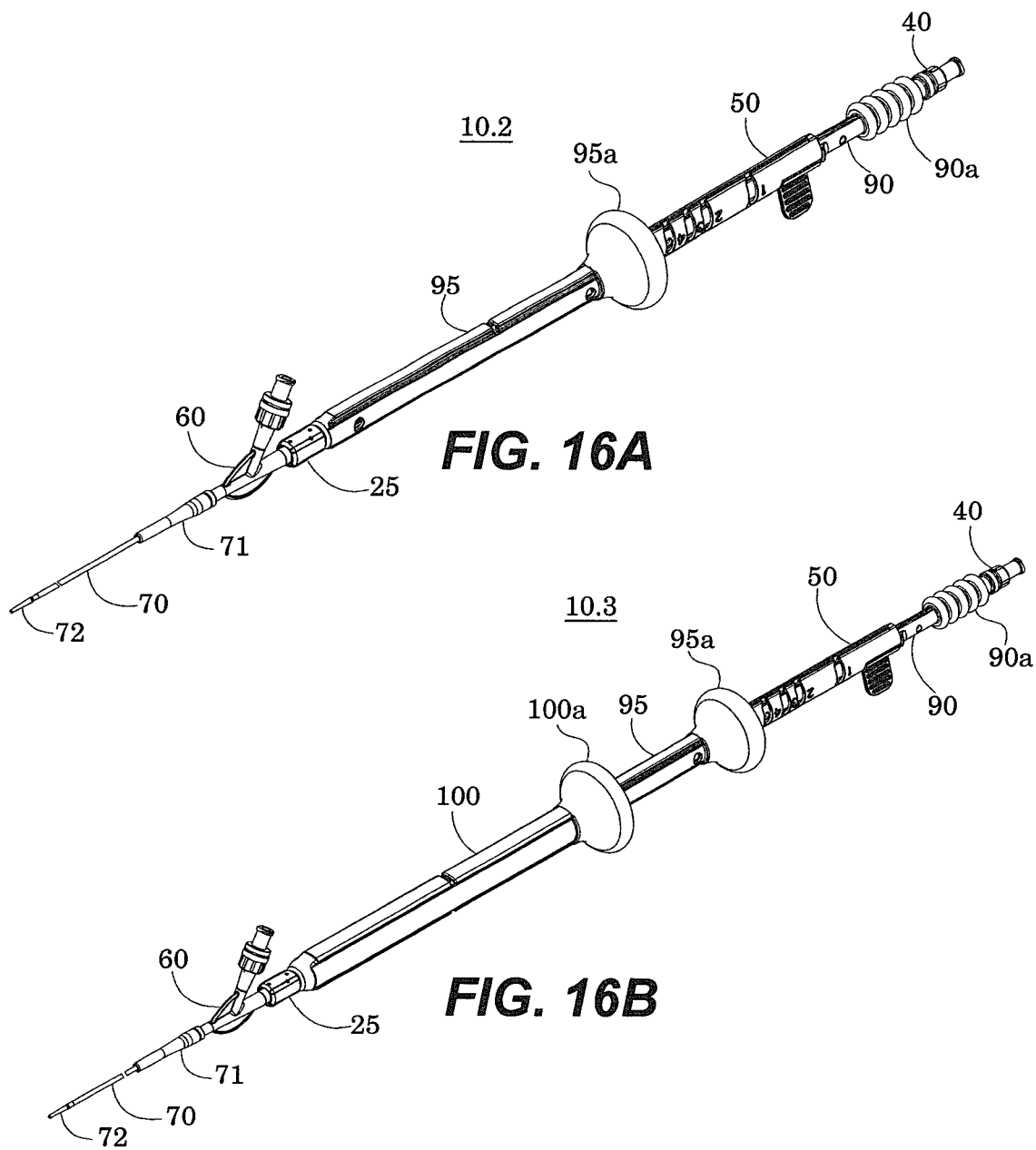

VARIABLE SCALE STENT DEPLOYMENT DEVICE

This application is a Continuation of application Ser. No. 14/858,881, filed on Sep. 18, 2015, which is a Continuation-in-Part of U.S. patent application Ser. No. 12/545,982, filed on Aug. 24, 2009, now U.S. Pat. No. 9,439,652. The entirety of the aforementioned application is incorporated herein by reference.

FIELD

This application generally relates to medical devices. In particular, the application relates to a delivery system for introducing implantable medical devices into a body cavity.

BACKGROUND

Implants may be placed in the human body for a variety of reasons. For example, stents are placed in a number of different body lumens such as blood vessels and biliary ducts; vena cava filters are implanted in the vena cava to catch thrombi sloughed off from other sites within the body; and vaso-occlusive devices are used for the treatment of intravascular aneurysms. Interventional practitioners, regardless of subspecialty have always had to demonstrate profound dexterity in order to effectively and accurately perform invasive procedures. This is particularly the case with the delivery and deployment of implantable devices where there is very little room for error with respect to placement. In order to assist with placement accuracy, many practitioners utilize scopes, such as bronchoscopes or endoscopes, ultrasound, CT scanning, or other imaging modalities however, handling the imaging modality and the delivery catheter can often be a clumsy process when the two devices easily disassociate from each other. Moreover, since many delivery catheters, for one reason or another, cannot be adequately managed with one hand, additional personnel are required when handling the scope and the delivery catheter. Therefore, there is an existing need for a delivery system that allows a physician to deploy an implantable device with one hand. Furthermore the additional need for a device that can be easily adapter to handle varying French scale catheters is important.

In view of the foregoing disadvantages inherent in conventional deployment systems, the invention provides a novel system and method for deployment of implantable devices.

SUMMARY

One aspect of the present application directs to a variable scale stent deployment device comprising: a variable inner diameter scale sleeve insert, a base handle comprising a base tubular member with a central longitudinal lumen, a proximal palm rest handle and a deployment extension, and a first tubular member having a first tubular body with a distal floating luer fitting and a first handle, wherein the base tubular member has a proximal end and a distal end, wherein the variable inner diameter scale sleeve insert is inserted into central longitudinal lumen of the base tubular member from the proximal end of the base tubular member, and wherein the first tubular member slides over the base tubular member of the base handle from the distal end of the base tubular member.

Another aspect of the present application is directed to a kit comprising the variable scale stent deployment device comprising: a variable inner diameter scale sleeve insert, a base handle comprising a base tubular member with a central longitudinal lumen, a proximal palm rest handle and a deployment extension, and a first tubular member having a first tubular body with a distal floating luer fitting and a first handle, wherein the base tubular member has a proximal end and a distal end, wherein the variable inner diameter scale sleeve insert is inserted into central longitudinal lumen of the base tubular member from the proximal end of the base tubular member, and wherein the first tubular member slides over the base tubular member of the base handle from the distal end of the base tubular member.

The application also directs to a method for implanting an implantable device into a body lumen of a subject in need thereof, comprising: attaching the proximal end of a catheter of the desired scale size to the variable scale stent deployment device, wherein the catheter comprises an implantable device at or near its distal end, establishing an entry portal, introducing the distal end of the catheter through the entry portal, advancing the catheter to the desired body lumen such that the implantable device is located in the desired location, and deploying the implantable device.

BRIEF DESCRIPTION OF THE DRAWINGS

The accompanying drawings illustrate one or more embodiments of the present application and, together with the written description, serve to explain the principles of exemplary embodiments of the present application.

FIGS. 2A & 2B show top plan and longitudinal section views of an embodiment of a primary trigger variable scale stent deployment device.

FIGS. 12A & 12B show top plan and longitudinal section views of an embodiment of a dual trigger variable scale stent deployment device.

FIGS. 16A & 16B are isometric views of the primary trigger and dual trigger spool embodiment's perspective of an embodiment of a variable scale stent deployment device.

DETAILED DESCRIPTION

Figure 1:
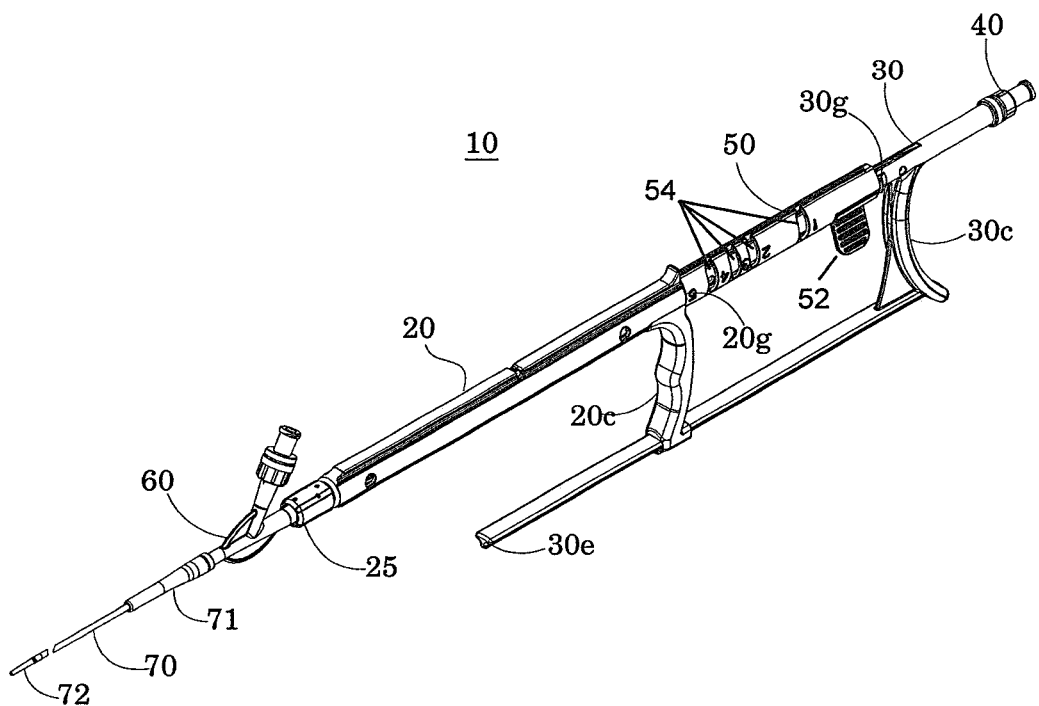
FIG. 1 is an isometric view of an embodiment of a primary trigger perspective of the variable scale stent deployment device.

The following detailed description is presented to enable any person skilled in the art to make and use the object of the present application. For purposes of explanation, specific nomenclature is set forth to provide a thorough understanding of the present application. However, it will be apparent to one skilled in the art that these specific details are not required to practice the object of the present application. Descriptions of specific applications are provided only as representative examples. The present application is not intended to be limited to the embodiments shown, but is to be accorded the widest possible scope consistent with the principles and features disclosed herein.

All publications, patents and patent applications referenced in this specification are herein expressly incorporated by reference to the same extent as if each individual publication or patent application was specifically and individually indicated by reference. In case of conflict between the present disclosure and the incorporated patents, publications and references, the present disclosure should control.

The phraseology and terminology used herein is for the purpose of description and should not be regarded as limiting. The use of "including," "comprising," or "having" and variations thereof herein is meant to encompass the items listed thereafter and equivalents thereof as well as additional items. "Comprising" also encompasses the terms "consisting of" and "consisting essentially of." The use of "consisting essentially of" means, e.g., that a method may include additional steps, but only if the additional steps do not materially alter the basic and novel characteristics of the claimed method. Unless specified or limited otherwise, the terms "joined," "mounted," "connected," "supported," and "coupled" and variations thereof herein are used broadly and encompass both direct and indirect mountings, connections, supports, and couplings. Further, "connected" and "coupled" are not restricted to physical or mechanical connections or couplings.

No admission is made that any reference, including any patent or patent document, cited in this specification constitutes prior art. In particular, it will be understood that unless otherwise stated, reference to any document herein does not constitute an admission that any of these documents forms part of the common general knowledge in the art in the United States or in any other country. Any discussion of the references states what the author asserts and the applicant reserves the right to challenge the accuracy and pertinence of any of the documents cited herein.

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

The present application relates to a delivery system for introducing implantable medical devices into a body cavity. Depending on the size of the orifice or opening in which the device is required to pass through determines the scale size of the device. As used herein, the term "scale" refers to a measurement of the diameter of the outside of a catheter or the inside of a lumen. The scale can be measured in any type of practicable unit including, but not limited to, metric, U.S. Customary Units, gauge, and French scale.

As used herein, "French scale," also known as "Charriere's system," relates to a system of measure of the external diameter of a catheter, not to the diameter of the internal channel. French sizing has uniform increments starting with 1 Fr with no upper end point. Each increment of French sizing equals 0.33 mm, for example, a 3 Fr catheter equals 1 mm outer diameter.

Unless otherwise noted, technical terms are used according to conventional usage. However, as used herein, the following definitions may be useful in aiding the skilled practitioner in understanding the application. Such definitions shall be applied, unless a different definition is given in the claims or elsewhere in this specification.

The full advantage of the variable scale stent deployment device in accordance with the application is realized when optimal scale deployment size and ergonomically simplified functionality combine to result in a superior system. Thus, these capabilities allows for the implant to be applied as effectively as possible while minimizing the challenging ergonomic issues communally associated with the current deployment devices and methods.

One aspect of the present application relates to a device for deploying an implantable medical device into a body lumen comprising a base member with a variable inner diameter (ID) sleeve insert that accommodates varying scale lumens, and luer end cap, having a base handle and a deployment extension (the handle), a first tubular member having a first tubular body with distal floating luer fitting and a first handle (primary trigger), and a second tubular member having a second tubular body with distal floating luer fitting and a second handle (dual trigger).

In some embodiments, the first tubular member (primary trigger) fits over the deployment extension and is longitudinally slidable over the deployment extension, and the second tubular member (dual trigger) fits over the first tubular member and is longitudinally slid able over the first tubular member (primary trigger).

In some embodiments, the distal ends of the deployment extension, the first tubular body, and the second tubular body are adapted to hold and deploy the implantable medical device. In some embodiments, the proximal end of the base member (handle) is configured to accept a sleeve insert which houses an internal rigid support tube and a luer fitting.

In some embodiments, the distal end of the first and second tubular members (triggers) has a floating luer lock connection that joins a luer hub with strain relief and outer sheath to the trigger. Internal workings include a rigid support tubr joined to an inner lumen with distally located positioning bands and a distal tip.

In some embodiments, the device comprises a handled base member and finger pull primary trigger configuration to better accommodate the shortened travel required to deploy a stent of <60 mm in length.

In other embodiments, the device comprises a handled base member and finger pull dual trigger configuration with a primary and a secondary trigger for deploying a stent of >60 mm in length.

In yet other embodiments, the device comprises a finger grip base member and spool pull primary trigger configuration for deploying a stent of <60 mm in length.

In yet other embodiments, the device comprises a finger grip base member and spool pull dual trigger for deploying a stent of >60 mm in length.

In all embodiments the device has the capability of accommodating varying French scale lumens/catheters.

Reference is now made to FIGS. 1-10 in which a variable scale stent deployment device of the application, generally designated by reference numeral 10, is shown.

Figure 4:
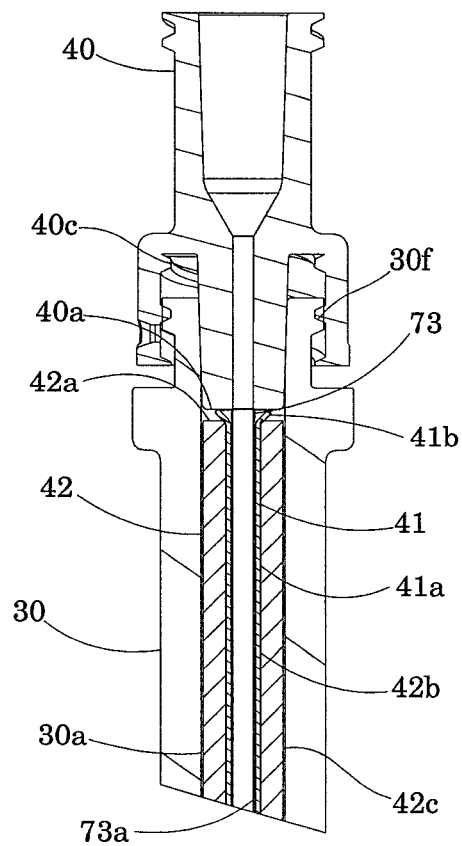
FIG. 4 is a scaled up partial detail view of the proximal area of the longitudinal section in FIG. 2.

One aspect of the present application relates to a variable scale stent deployment device 10 as shown in FIGS. 1 and 2A-B. In this embodiment, the device 10 has a primary trigger configuration comprising a handle 30, a luer end cap 40, a primary trigger 20 and a distal floating luer 25. The proximal end of the luer 25 is joined to a distal area 20a of the primary trigger 20 with two opposing pins 26 passing through groove 20b. The distal end of the luer 25 is connected to the proximal end of the luer hub 60 through a luer seal 61. The distal end of the Luer hub 60 is connected to a strain relief 71 which is connected to the outer sheath 70 and the tubular tip 72. As shown in FIG. 4, the handle 30 contains a tubular base 31 that holds a varying scale sleeve having a rigid support tube 41 having a body 41a, a flare 41b on one end of the body and an internal lumen 41c. The tube 41, together with lumen 30h of the handle 30 and inner lumen 73 on the distal end of the device 10, forms a lumen that allows for a guide wire to pass through the device 10.

A premature deployment prevention tab 50 (or safety tab 50) that rests against the proximal edge 20g of the primary trigger 20 and travel stop 30g of the handle 30 all elements comprised for deployment of a vascular implant. Pushing the safety tab release 52 from a lock position to an unlock position releases the safety tab 50. As shown in FIG. 1, the safety tab 52 may comprise a number of holes 54 on the tab body indicating where the safety tab 50 will be cut off for the applicable length of stent being deployed.

Figure 5A:
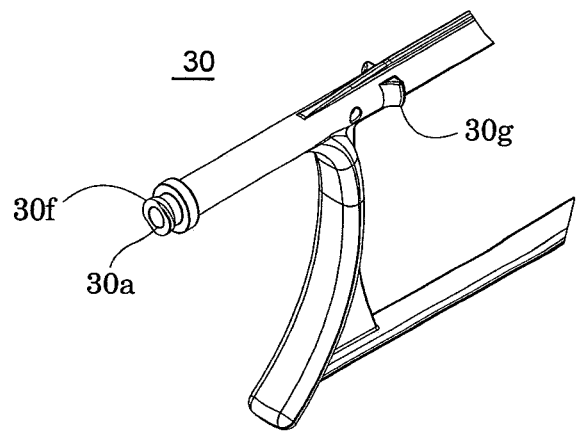
FIGS. 5A & 5B are isometric views of the proximal and distal perspectives of an embodiment of a base member having a base handle (the handle).
Figure 5B:
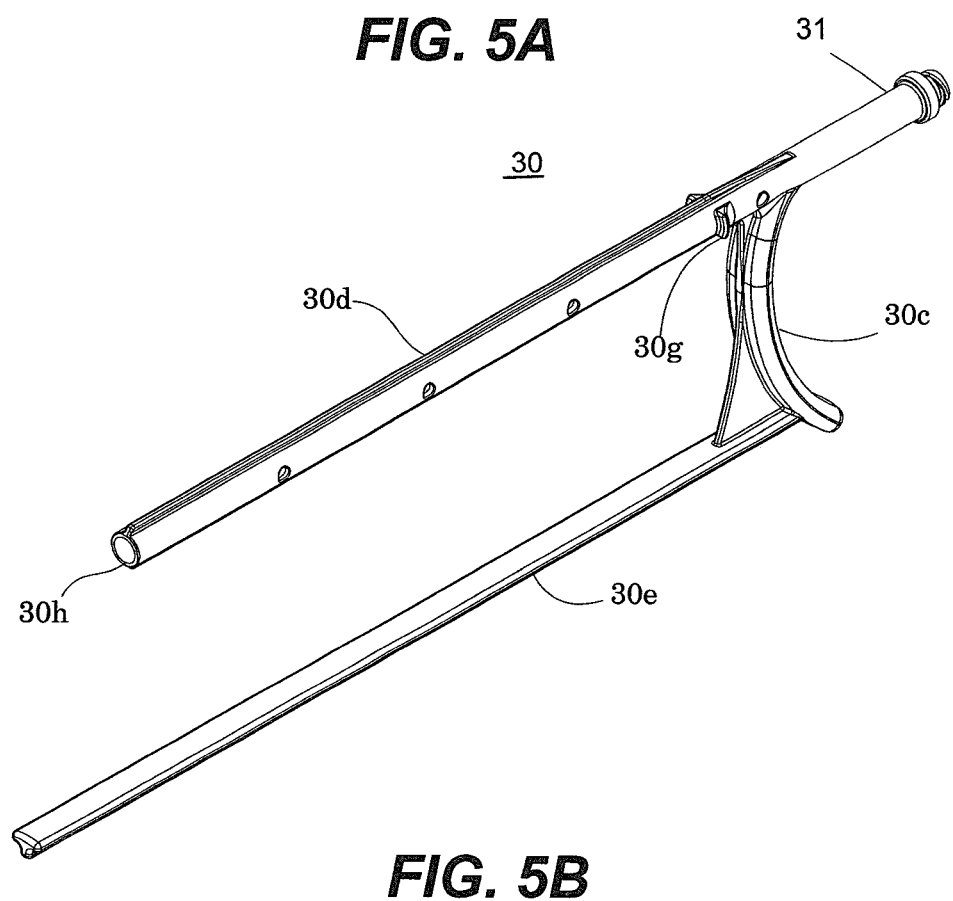

In an embodiment illustrated in FIGS. 5A-B, the handle 30 is defined by a tubular base member 31 having a central longitudinal lumen 30h and a proximal sleeve insert orifice 30a, a proximal palm rest handle 30c and a deployment extension 30d extending distally with a symmetrical travel stop 30g, and opposing slide arm 30e extending distally. As shown in FIGS. 2A-B and 4, the proximal sleeve insert orifice 30a accommodates a varying scale sleeve 42 resting on an internal edge/shoulder 30b (FIGS. 2A-B). The base member 31 contains at its proximal end a female luer fitting 30f. In one embodiment, the fitting 30f is in compliance with ISO 594-1 and -2 standard for 6% taper luer fittings.

Figure 6A:
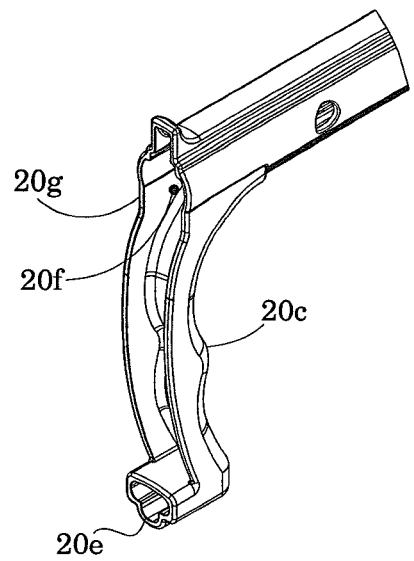
FIGS. 6A & 6B are isometric views of the proximal and distal perspectives perspective of an embodiment of a first tubular member (primary trigger).
Figure 6B:
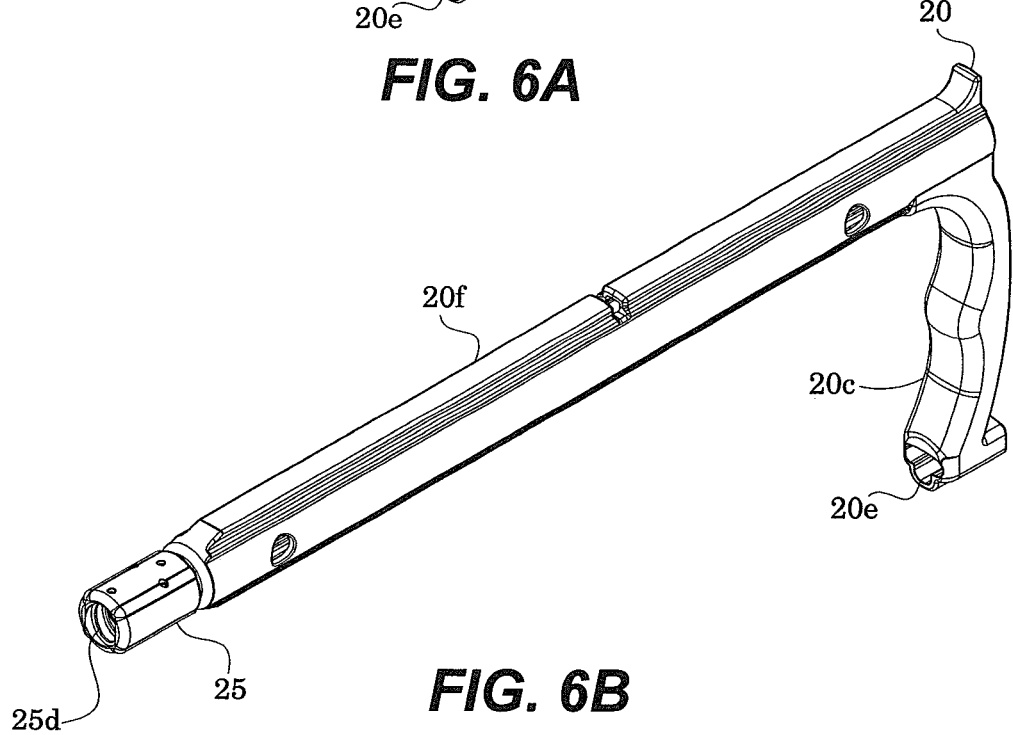
Figure 7A:
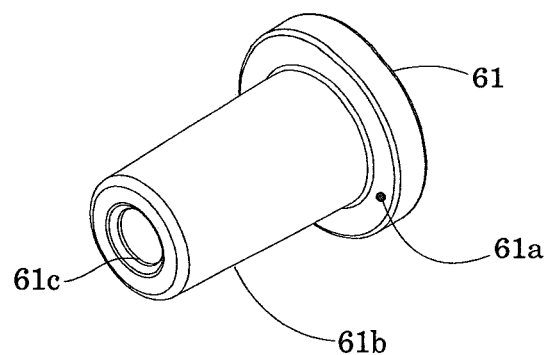
FIGS. 7A & 7B are isometric views of the proximal and distal perspectives of an embodiment of a luer seal insert.
Figure 7B:
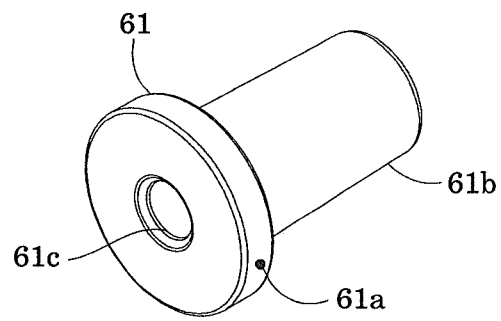

The primary trigger 20, detailed in FIGS. 6A-B, is composed of a distally extending tubular body 20f, a proximal finer pull 20c with slide orifice 20e, a proximal travel stop surface 20g, and a distal floating luer fitting 25 with luer threads 25d in compliance with ISO 594-1 and -2 standard for 6% taper luer fittings. The slide orifice 20e accommodates the slide 30e of handle 30. The travel stop surface 20 contacts the travel stop 30g of handle 30 and stops the movement of handle 30.

Figure 3:
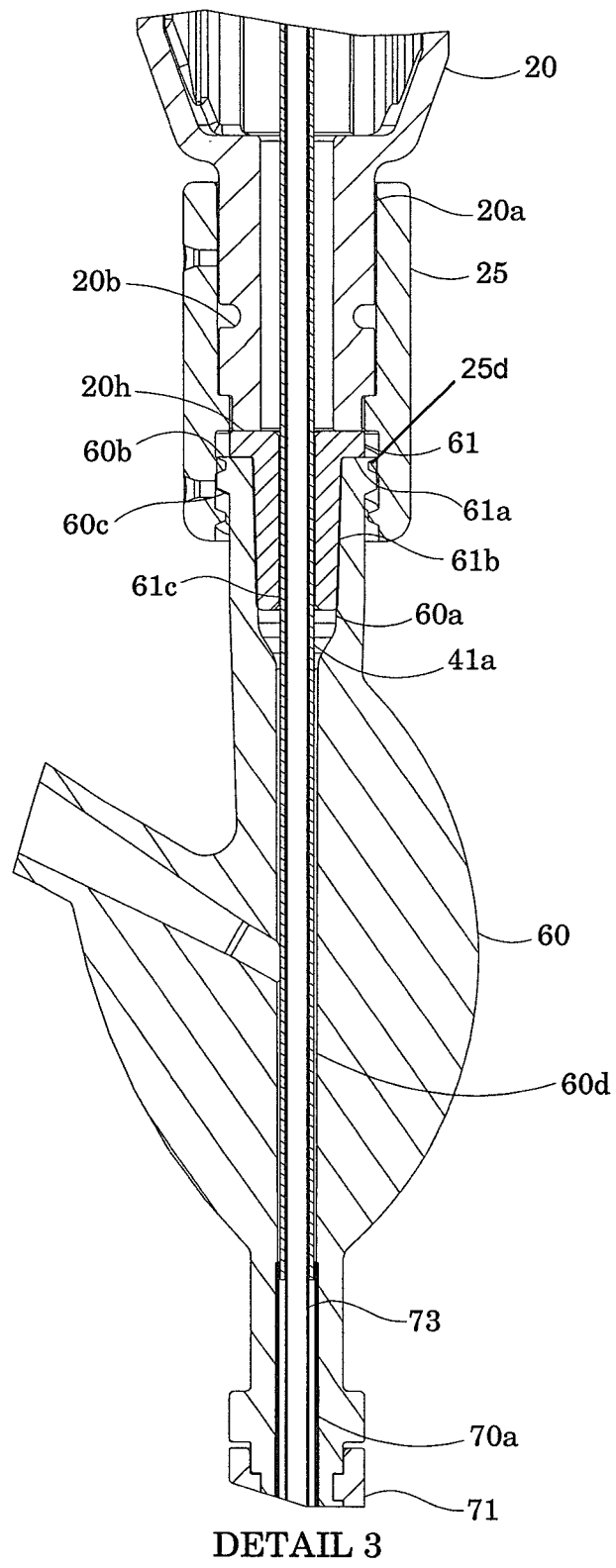
FIG. 3 is a scaled up partial detail view of the distal area of the longitudinal section in FIG. 2.

As shown in more detail of an embodiment in FIG. 3, luer hub 60 is connected to the distal floating luer 25 of the primary trigger 20. The hub thread 60c is configured per ISO 594-1 and -2 and mates with the luer threads 25d. The luer hub 60, as exemplified, is joined with the outer sheath 70 and strain relief 71 and travels as a comprised unit when joined with the primary trigger 20. The primary trigger 20 is retracted by pulling the finger pull 20c in a proximal linear motion over the handle extension 30d and slide arm 30e with the proximal edge 20g coming to rest up against the handle stop 30g in a fully deployed position (see FIGS. 1 and 2A-B).

As shown in more detail in FIG. 4, in one embodiment the internal elements of the device are comprised of the inner lumen 73 joined to the rigid support tube 41 and distal tip 72, the shaft 42c of the variable ID scale sleeve insert 42 inserted in the longitudinal orifice 30a and seated with the shoulder 30b of the handle 30. The taper 61b of the luer hub seal 61 is seated in the luer hub cavity 60a and the flange 61a of the luer seal 61, shown in FIG. 7, confined between the proximal surface 60b of the luer hub 60 and the distal edge 20h of the primary trigger 20.

The inner lumen 73 extends distally from the proximal flare 41b of the rigid support tube 41, through the internal lumen 41c of the rigid support tube 41, to the tip 72 (FIG. 2). The rigid support tube 41a traverses through the longitudinal orifice 42b of the varying scale sleeve 42 and through orifice 30h of the handle 30 (see FIGS. 5A-B), continuing through the tubular body 20f of the primary trigger 20, continuing through the central longitudinal orifice 61c (see FIG. 3) of the luer seal 61, and through the longitudinal channel 60d of the hub 60 with the rigid support lumen terminating just distal of the hub channel 60d while the inner lumen 73 continues through the lumen channel 70a of the outer sheath 70 terminating distal of the most distal edge of the outer sheath and joining at the distal tip 72 (see FIGS. 1 and 2A-B).

Figure 9:
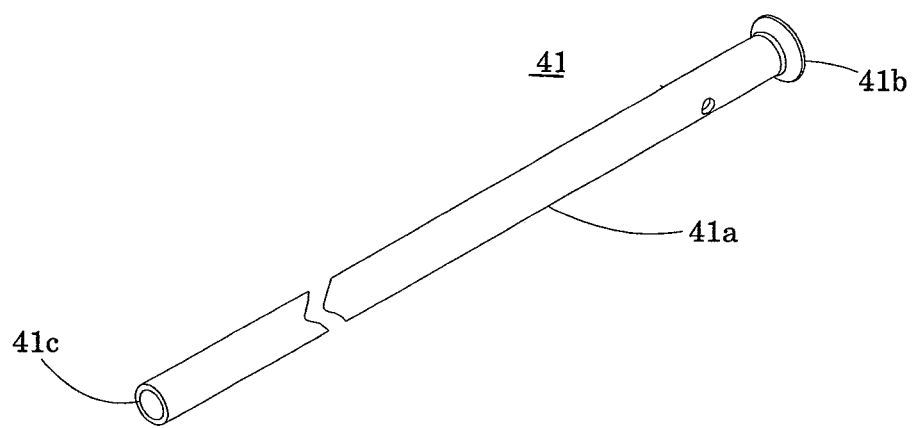
FIG. 9 is an isometric view of an embodiment of a central lumen support.

The luer thread 40c of the luer end cap 40 is joined to the proximal luer thread 30f of the handle 30; the distal surface 40a of the luer end cap joins with the proximal flare 41b of the rigid support tube 41 shown in FIG. 9. Tightening the cap 40 compresses the proximal surface 42a of the variable ID scale sleeve insert 42, detailed in FIG. 10, against the proximal flare 41b in turn compressing the distal surface 42d against the shoulder 30b (FIGS. 2A-B) of the handle 30 thus securing the joined internal components within the handle 30.

Figure 8A:
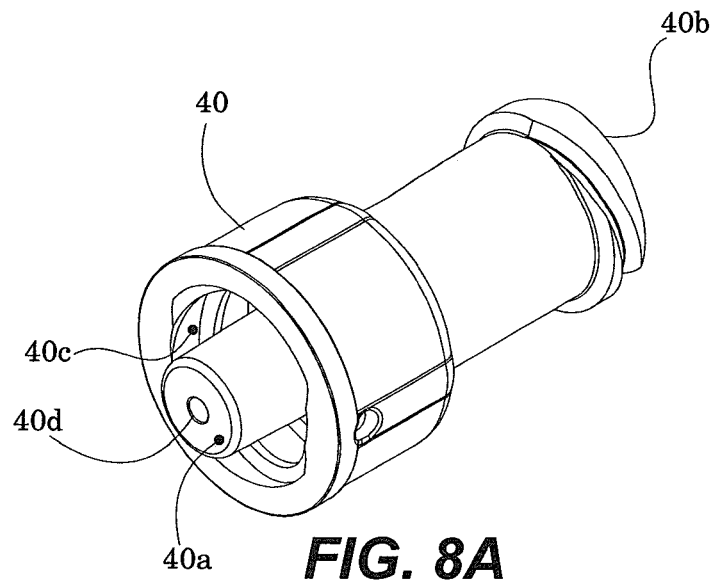
FIGS. 8A & 8B are isometric views of the proximal and distal perspectives of an embodiment of a luer end cap fitting.
Figure 8B:
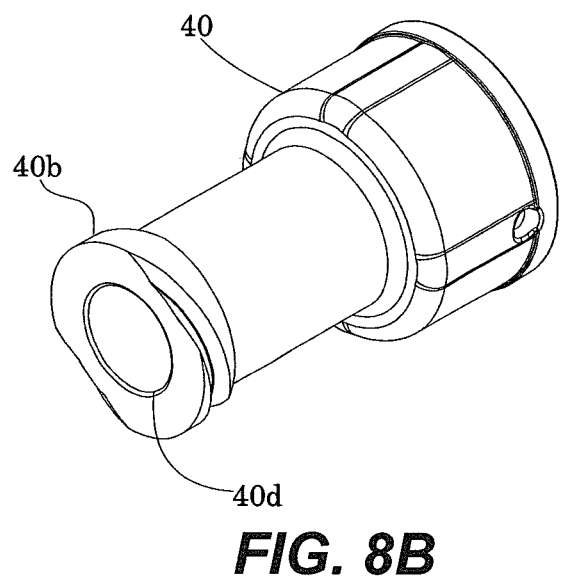

As detailed in FIG. 8, the central longitudinal orifice 40d of the luer end cap 40 aligns with the internal lumen 41c (FIG. 9) of the rigid support tube 41 and the central orifice 73a of the inner lumen 73 (FIG. 4). This allows for the passage of a guide wire through the device. Further, again turning to FIGS. 8A-B, the proximal female luer 40b of the end cap 40 provides a connection fitting for auxiliary devices e.g. syringe.

Figure 10:
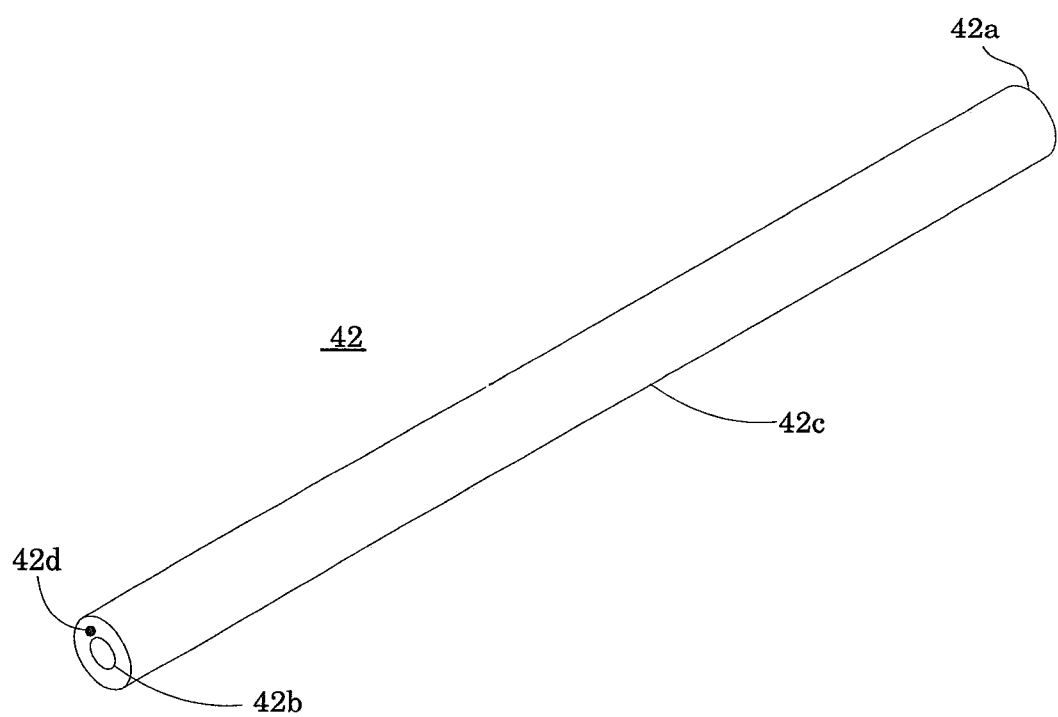
FIG. 10 is an isometric view of an embodiment of a central adapter sleeve.

The variable ID scale sleeve insert 42 shown in FIG. 10 is an interchangeable element of the device. The external diameter of the varying scale sleeve 42 is such that it fits securely within the longitudinal lumen 30h of base member 31. The diameter of the internal channel 42b of the variable ID scale sleeve insert 42 is selected by a practitioner to accommodate the rigid support tube 41 which, in turn, has an internal lumen 41c to accommodate a catheter having a desired scale size. The rigid support tube 41 is inserted into the internal channel 42b of the of the variable ID scale sleeve insert 42. In some embodiments, the rigid support tube 41 has an internal lumen 41c of a diameter measured in French scale units and selected from 1 Fr, 2 Fr, 3 Fr, 4 Fr, 5 Fr, 6 Fr, 7 Fr, 8 Fr, 9 Fr, 10 Fr, 11 Fr, 12 Fr, 13 Fr, 14 Fr, 15 Fr, 16 Fr, 17 Fr, 18 Fr, 19 Fr or 20 Fr. In other embodiments, the rigid support tube 41 has a an internal lumen 41c of a diameter measured of a diameter in French scale units of between 1 Fr and 50 Fr. In some embodiments, the varying scale sleeve 42 is made of a rigid material, such as acrylonitrile butadiene styrene.

FIGS. 11-15B show another embodiment of a variable scale stent deployment device of the present application. In some embodiments, the configuration of a primary trigger shares many features shown in FIGS. 1-10, but can optionally be configured as a dual trigger combination depending on device travel requirements for deployment of a vascular implant. Device 10.1 exemplifies a dual trigger (primary and secondary) configuration allowing increased deployment travel while maintaining a single handed operation.

Figure 11:
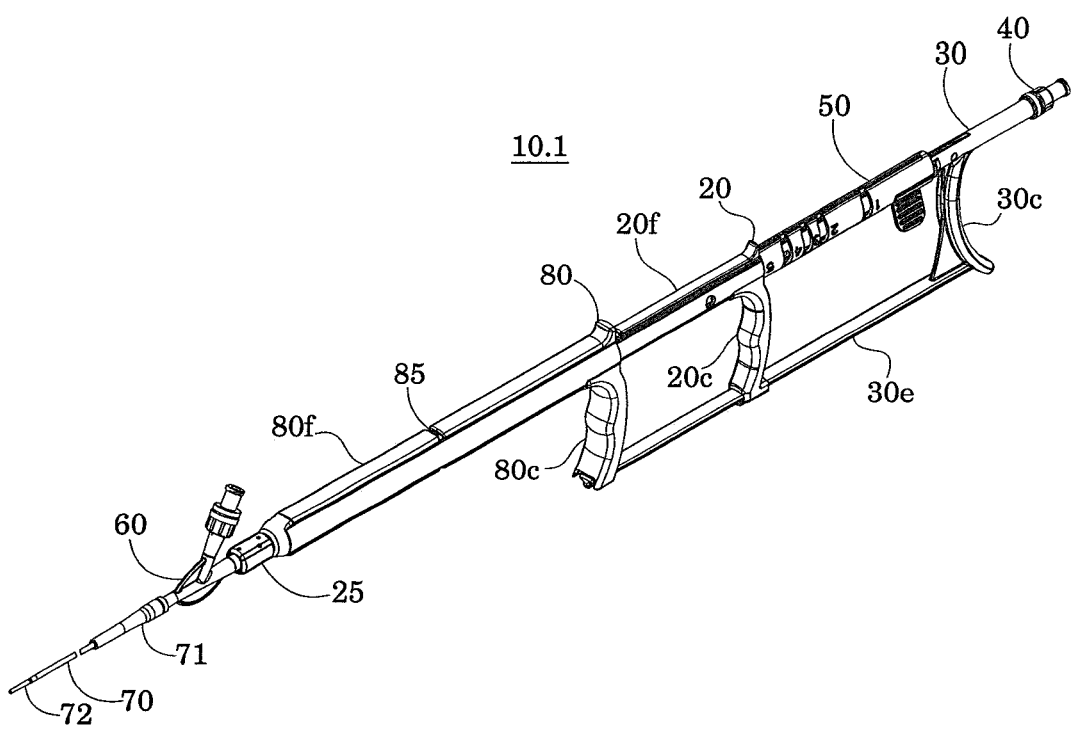
FIG. 11 is an isometric view of the dual trigger perspective of an embodiment of a variable French scale stent deployment device.

In some embodiments, as shown in FIGS. 11 and 12A-B, the device comprises a handle 30 with luer end cap 40, a primary trigger 20, and a secondary trigger 80 with distal floating luer 25 joined in the distal area 80a with two opposing pins 26 passing through groove 80b. Joined to 25 of the secondary trigger 80 is a luer seal 61 and a luer hub 60, strain relief 71 and outer sheath 70, joined to luer thread 25d of floating luer 25 of the primary trigger 20 by luer thread 85c of the retractor tab 85, internally a variable ID scale sleeve 42, a rigid support tube 41 and inner lumen 73 with a tubular tip 72. In particular embodiments, a premature deployment prevention safety tab 50 rests against the proximal edge 20g of the primary trigger 20 and travel stop 30g of the handle 30.

In an illustrated embodiment; the handle 30 is defined by a base member 31 with a central longitudinal lumen 30h having a proximal sleeve insert orifice 30a that accommodates a varying scale sleeve 42 within a rigid support tube 41 resting on an internal edge/shoulder 30b. In some embodiments, the proximal male luer fitting 30f is in compliance with ISO 594-1 and -2 standards for 6% taper luer fittings. In some embodiments, the handle 30 comprises a proximal palm rest handle 30c and a deployment extension 30d extending distally with a symmetrical travel stop 30g and opposing slide arm 30e extending distally.

The primary trigger 20 with a distally extending tubular body 20f a proximal finger pull 20c with slide orifice 20e which accommodates the slide 30e of handle 30, a proximal travel stop surface 20g which contacts the travel stop 30g of handle 30, and a distal floating female luer fitting 25 with female threads 25d in compliance with ISO 594-1 and -2 standard for 6% taper luer fittings. In this embodiment, both the primary trigger 20 and the secondary trigger 80 comprise a distal luer fitting. The primary trigger 20 now holds the retractor and the secondary trigger 80 holds the Y-hub and seal.

As shown in FIGS. 12A-B and 14A-B, the secondary trigger 80 comprises a distally extending tubular body 80f a proximal finger pull 80c with slide relief 80e which accommodates the slide 30e of handle 30, and a distal floating female luer fitting 25 with female threads 25d in compliance with ISO 594-1 and -2 standard for 6% taper luer fittings. Joined to the distal floating female luer 25 mated to the secondary trigger 80 is the luer hub 60. The hub thread 60c configured per ISO 594-1 and -2 mates with the luer threads 25d, the luer hub as illustrated in FIGS. 12A-B is joined with the outer sheath 70 and strain relief 71 and which travels as a unit when joined with the secondary trigger 80.

The primary trigger 20 with joined retractor tab 85 is inserted in the tubular opening 80f of the secondary trigger 80 and located with the retractor tab arms 85a and 85b resting in the orifices 80g and 80h of the secondary trigger 80. The retractor tab arms 85a and 85b grip the secondary trigger as it is retracted by pulling the finger pull 20c of the primary trigger 20 in a proximal linear motion over the handle extension 30d and slide arm 30e with the proximal edge 20g coming to rest up against the handle stop 30g in a fully retracted position. The retractor tab arms 85a and 85b (see FIG. 13) compress as the secondary trigger is retracted by pulling the finger pull 80c (see FIGS. 14A-B) in a proximal linear motion over the primary trigger extension 20f and slide arm 30e with the proximal inner surface 80h coming to rest up against the finger pull 20c of the primary trigger 20 in a fully deployed position.

The internal elements of the device are comprised of the inner lumen 73 which includes the internal lumen 41c of the rigid support tube 41 and distal tip 72, the shaft 42c of the variable ID scale sleeve 42 inserted in the longitudinal orifice 30a and seated with the shoulder 30b of the handle 30. The taper 61b of the luer hub seal 61 seated in the luer hub cavity 60a and the flange 61a of the luer seal 61 is confined between the proximal surface 60b of the luer hub 60 and the distal edge 80h of the secondary trigger 80. As in FIG. 4, described above, the inner lumen 73 extends from the proximal flare 41b of the rigid support tube 41 distally and joins to the tip 72.

Figure 13:
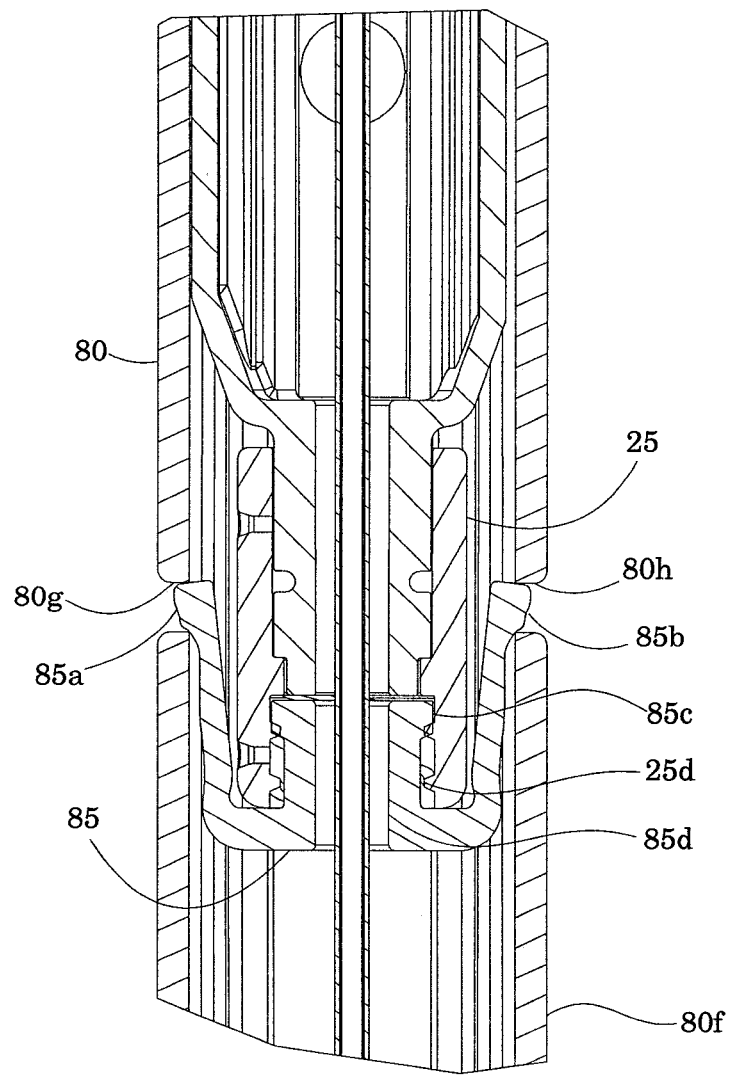
FIG. 13 is a scaled up partial detail view of the distal area of the longitudinal section in FIG. 12.
Figure 14A:
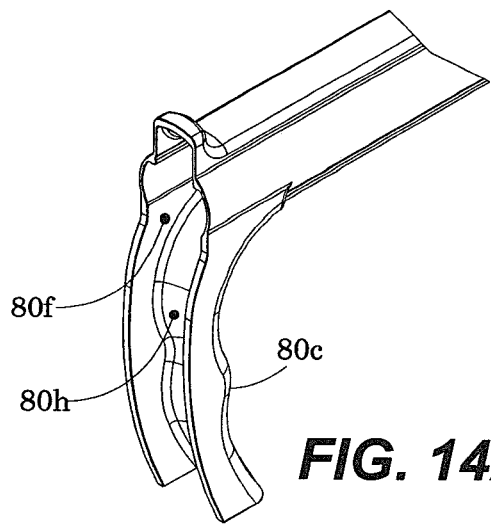
FIGS. 14A & 14B are isometric views of the proximal and distal perspectives of an embodiment of a secondary tubular member (secondary trigger).
Figure 14B:
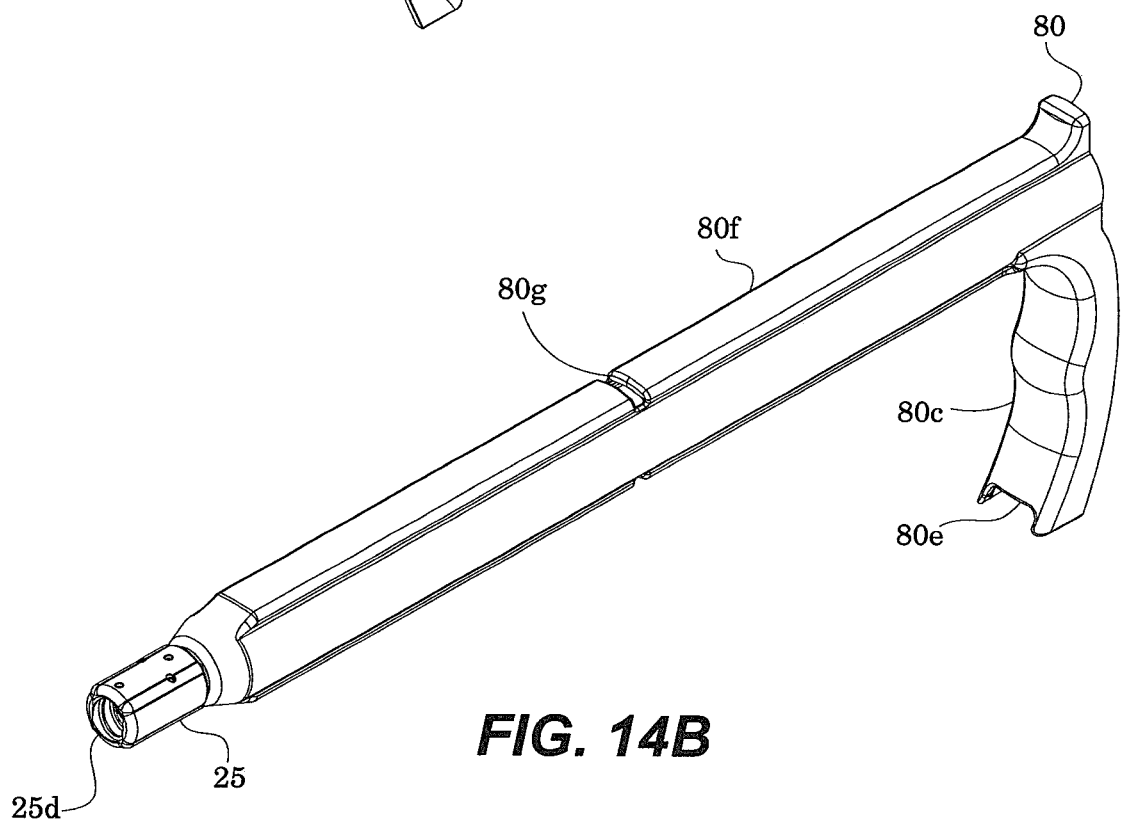
Figure 15A:
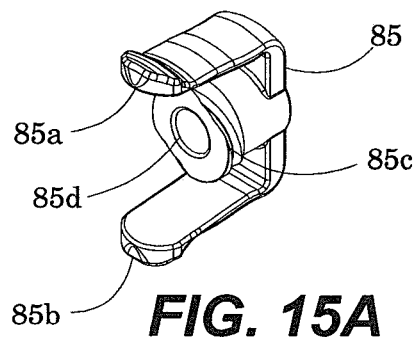
FIGS. 15A & 15B are isometric views of the proximal and distal perspectives of an embodiment of a dual trigger retractor tab.
Figure 15B:
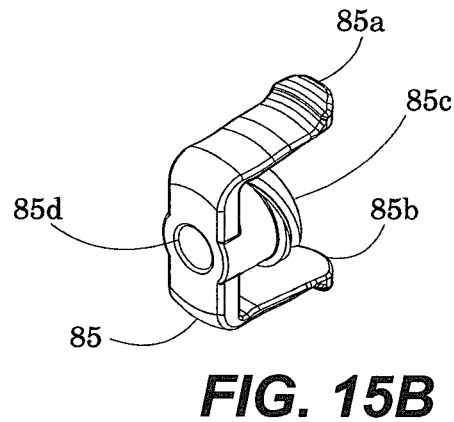

As shown in FIGS. 2A-B, described above, the inner lumen of the device traverses through the longitudinal orifice 42b of the variable ID scale sleeve insert 42 and through orifice 30h of the handle 30, continuing through the tubular body 20f of the primary trigger 20 and orifice 85d of the retractor tab 85 (see FIGS. 13 and 15A-B). The lumen continues through the tubular body 80f of the secondary trigger 80 (FIGS. 14A-B), the central longitudinal orifice 61c of the luer seal 61 (FIGS. 11 and 12A-B), and through the longitudinal channel 60d of the hub 60 with the rigid support lumen, terminating just distal of the hub channel 60d, while the inner lumen 73 continues through the lumen channel 70a of the outer sheath 70 terminating distal of the most distal edge of the outer sheath 70 and joining at the distal tip 72.

The luer thread 40c of the luer end cap 40 is joined to the proximal luer thread 30f of the handle 30 (see FIG. 4). The distal surface 40a of the luer end cap joins with the proximal flare 41b of the rigid support tube 41 tightening the cap 40 compresses the proximal surface 42a of the variable ID scale sleeve insert 42 against the proximal flare 41b in turn compressing the distal surface 42d against the shoulder 30b of the handle 30 thus securing the joined internal components within the handle 30, as shown in previously described FIG. 2. The central longitudinal orifice 40d of the luer end cap 40 (FIGS. 8A-B) aligns with the central orifice 73a of the inner lumen 73 (FIG. 4) allowing for the passage of a guide wire, the proximal female luer 40b of the end cap 40 provides a connection fitting for auxiliary devices e.g. syringe.

Reference is now made to FIGS. 16A-B, in which yet another two embodiments of a variable French scale stent deployment device, generally designated by reference numeral 10.2 and 10.3, in accordance with the invention are shown. Device 10.2 is of a primary pull configuration, while 10.3 has a dual pull configuration allowing for increased deployment travel. These two embodiments differ from embodiments 10 and 10.1 mainly in the configuration of the finger pulls 80c and 20c of the primary trigger 20 and secondary trigger 80, respectively. The handle 30 differs in respect to the palm rest 30c, internal workings in all embodiments are identical to embodiments 10 and 10.1. Device 10.2 primary pull comprised of a primary deployment pull 95 with a proximal flare pull 95a and primary deployment extension 90 with finger grip 90a. Device 10.3 dual pull comprised of a primary deployment pull 95 with a proximal flare pull 95a, a secondary deployment pull 100 with a proximal flare pull 100a, and primary deployment extension 90 with finger grip 90a. in some embodiments, two-handed operation is contemplated.

Kit

Another aspect of the present application relates to a kit comprising a variable scale stent deployment device. In some embodiments, the device comprises a variable ID French scale sleeve insert for insertion into the device, a base handle and a deployment extension, a first tubular member having a first tubular body with a distal floating luer fitting and a first handle, wherein the first tubular member slides over the base handle. In some further embodiments, the device further comprises a second tubular member having a second tubular body with a distal floating luer fitting and a second handle, wherein the second tubular body slides over the first tubular body.

In some embodiments, the kit comprises a catheter.

In another embodiment, the kit comprises a guide wire.

In still another embodiment, the kit comprises a plurality of variable ID scale sleeve inserts for insertion into the variable scale stent deployment device, the variable ID scale sleeve inserts having internal channels of different diameters to accommodate catheters of different scale sizes.

In yet another embodiment, the kit comprises an implantable device for insertion into a body lumen. In a further embodiment, the implantable device is a stent.

Method

Another aspect of the present application relates to a method for inserting an implantable device in a desired body lumen of a subject in need thereof using a variable scale stent deployment device. In some embodiments, the device comprises a variable ID French scale sleeve insert for insertion into the device, a base handle and a deployment extension, a first tubular member having a first tubular body with a distal floating luer fitting and a first handle, wherein the first tubular member slides over the base handle. In some further embodiments, the device further comprises a second tubular member having a second tubular body with a distal floating luer fitting and a second handle, wherein the second tubular body slides over the first tubular body.

The method comprises attaching the proximal end of a catheter of the desired scale size to the variable scale stent deployment device, wherein the catheter comprises an implantable device at or near its distal end. In some embodiments, the catheter is glued to the Y-Hub which is attached via the distal lure. In some further embodiments, the implantable device is a stent. In some still further embodiments, the stent is a self-expanding stent.

The method further comprises establishing an entry portal and introducing the distal end of the catheter comprising an implantable device at or near its distal end through the entry portal. The catheter is advanced to the desired body lumen such that the implantable device is located in the desired location.

In some embodiments, the implantable device is deployed by pulling the first handle of the first tubular member in a proximal direction, thereby sliding the first tubular member in a proximal direction over the base handle thereby resulting in deployment of the implantable device.

In other embodiments, the sliding of the first tubular member results in a partial deployment of the implantable device, such as when the implantable device is of great length. Accordingly, a variable scale stent deployment device comprising a second tubular member having a second tubular body with a distal floating Luer fitting and a second handle, wherein the second tubular body slides over the first tubular body. The implantable device is partially deployed by pulling the first handle of the first tubular member in a proximal direction, thereby sliding the first tubular member in a proximal direction over the base handle. The second handle of the second tubular member is then pulled in a proximal direction, thereby sliding the second tubular member proximally over the first tubular member, thereby resulting in deployment of the implantable device.

Exemplary body lumens treatable with the device and methods of the present application include, but are not limited to, the aorta, the superior vena cava, the inferior vena cava, coronary artery, pulmonary artery, pulmonary vein, carotid artery, jugular vein, biliary tract, colorectal tract, esophageal tract, ureteral tract, urethral tract, or upper airway. Exemplary conditions treatable with the device and methods of the present application include, but are not limited to, aneurism, fistula, thrombus, laceration and plaque formation.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A variable scale medical implant deployment device, comprising:
   a variable inner diameter (ID) scale sleeve insert,
   a base handle comprising a base tubular member with a central longitudinal lumen, a proximal palm rest handle, a slide arm and a deployment extension, and
   a first tubular member having a first tubular body with a distal floating luer fitting and a first trigger,
   wherein the base tubular member has a proximal end and a distal end,
   wherein the variable ID scale sleeve insert is inserted into central longitudinal lumen of the base tubular member from the proximal end of the base tubular member,
   wherein the first tubular member slides over the base tubular member of the base handle from the distal end of the base tubular member, and
   wherein the first trigger is retractable along the slide arm of the base handle by pulling a first finger pull of the first trigger.

2. The device of claim 1, further comprising:
   a second tubular member having a second tubular body with a distal floating luer fitting and a second trigger, wherein the second tubular body slides over the first tubular body,
   wherein the second trigger is retractable along the slide arm of the base handle by pulling a second finger pull of the second trigger.

3. The device of claim 1, wherein the variable ID scale sleeve insert is a replaceable insert and has an external diameter that allows the variable ID scale sleeve insert fits securely within the central longitudinal lumen of the base handle.

4. The device of claim 1, wherein the variable ID scale sleeve insert comprises an internal channel with an inner diameter.

5. The device of claim 4, wherein the variable ID scale sleeve is made of a rigid material.

6. The device of claim 1, wherein the variable II) scale sleeve insert further comprises rigid support tube that is inserted into the internal channel of the variable ID scale sleeve, wherein the rigid support tube comprises a tube body and an internal lumen.

7. The device of claim 6, wherein the internal lumen of the rigid support has a diameter that accommodates a catheter.

8. The device of claim 6, wherein the internal lumen of the rigid support has a diameter in the range of 1-20 in French scale.

9. The device of claim 8, wherein the internal lumen of the rigid support has a diameter in the range of 3-15 in French scale.

10. The device of claim 1, wherein the variable ID scale sleeve insert is secured in the central longitudinal lumen of the base handle by an end cap at a proximal end of the central longitudinal lumen.

11. The device of claim 1, further comprising a safety tab that prevents premature deployment of a medical implant.

12. The device of claim 1, wherein the device is configured to insert a medical implant into a body lumen, the medical implant is a stent.

13. A kit comprising variable scale medical implant deployment device of claim 1.

14. The kit of claim 13, further comprising a catheter.

15. The kit of claim 13, further comprising a guide wire.

16. The kit of claim 13, wherein the variable inner diameter (ID) scale sleeve insert is one of a plurality of variable ID scale sleeve inserts for insertioninto the variable scale stent deployment device.

17. The kit of claim 13, further comprising one or more medical implants for insertion into a body lumen.

* * * * *